US008834387B2

(12) United States Patent
Platt

(10) Patent No.: US 8,834,387 B2
(45) Date of Patent: Sep. 16, 2014

(54) DETECTION OF AIRWAY RESISTANCE

(75) Inventor: Ronald S. Platt, Calgary (CA)

(73) Assignee: Sagatech Electronics Inc., Calgary (CA)

( * ) Notice: Subject to any disclaimer, the term of this patent is extended or adjusted under 35 U.S.C. 154(b) by 800 days.

(21) Appl. No.: 12/139,176

(22) Filed: Jun. 13, 2008

(65) Prior Publication Data
US 2009/0306530 A1  Dec. 10, 2009

(51) Int. Cl.
*A61B 5/08* (2006.01)

(52) U.S. Cl.
USPC ........... 600/538; 600/529; 600/532; 600/534; 600/535; 600/536

(58) Field of Classification Search
USPC ..................... 600/529, 532, 534, 535, 536
See application file for complete search history.

(56) References Cited

U.S. PATENT DOCUMENTS

| | | | |
|---|---|---|---|
| 4,655,213 A | 4/1987 | Rapoport et al. | |
| 5,335,654 A | 8/1994 | Rapoport et al. | |
| 5,490,502 A | 2/1996 | Rapoport et al. | |
| 5,535,739 A | 7/1996 | Rapoport et al. | |
| 5,546,933 A | 8/1996 | Rapoport et al. | |
| 5,704,345 A | 1/1998 | Berthon-Jones | |
| 5,803,066 A | 9/1998 | Rapoport et al. | |
| 6,029,665 A | 2/2000 | Berthon-Jones | |
| 6,138,675 A | 10/2000 | Berthon-Jones | |
| 6,286,508 B1 | 9/2001 | Remmers et al. | |
| 6,363,933 B1 | 4/2002 | Berthon-Jones | |
| 6,550,478 B2 | 4/2003 | Remmers et al. | |
| 6,814,073 B2 | 11/2004 | Wickham | |
| 6,920,877 B2 | 7/2005 | Remmers et al. | |
| 7,013,893 B2 * | 3/2006 | Wickham et al. | 128/204.23 |
| 7,159,588 B2 | 1/2007 | Wickham | |
| 2005/0241639 A1 * | 11/2005 | Zilberg | 128/204.21 |
| 2008/0119755 A1 * | 5/2008 | Schatzl et al. | 600/538 |

FOREIGN PATENT DOCUMENTS

| | | | |
|---|---|---|---|
| WO | WO2005051470 | * | 6/2005 |
| WO | WO2006045559 | * | 5/2006 |

OTHER PUBLICATIONS

Guler et al, Two-stage classi(cation of respiratory sound patterns, 2005, Computers in Biology and Medicine, 35, pp. 67-83.*
Huang, Y., et al., "Computational simulation of human upper airway collapse . . . etc.", Journal of Applied Physiology, 2005, vol. 99, pp. 1138-1148.
Isono S., Feroah T.R., Hajduk E.A., Brant R., Whitelaw W.A., Remmers J.E., Interaction of cross-sectional area, driving pressure, and airflow of passive velopharynx, J Appl Physiol., 1997, 83:851-859.

\* cited by examiner

*Primary Examiner* — Narayan Bhat

(57) ABSTRACT

An airflow signal corresponding to the breathing of the patient is obtained. A section corresponding to inspiration, having a front portion and a middle portion, is found within the airflow signal. A peak value of the front portion is found, which is compared with a value representing the airflow of the middle portion. The presence of resisted breathing is determined based on the comparison between the peak value of the front portion with a value representing the airflow of the middle portion. A baseline value of the airflow signal is found by calculating the mode of values within an airflow signal representing the pressure within a patient's naris. The section corresponding to inspiration is determined by finding peak inspiration and baseline values within a breath and searching from the peak until the baseline is reached to find the section of inspiration.

13 Claims, 5 Drawing Sheets

US 8,834,387 B2

DETECTION OF AIRWAY RESISTANCE

TECHNICAL FIELD

This relates to the field of detection of airway resistance.

BACKGROUND

Sleep disordered breathing is a common disorder. There are two categories of respiratory disturbances during sleep, both of which result from narrowing of the pharyngeal airway. The first is sleep apnea which is manifested by transient respiratory disturbances such as apnea or hypopnea. The second is high upper airway resistance which, by contrast, is a sustained respiratory disturbance that causes obstructive hypoventilation. In high upper airway resistance, a segment of the pharynx displays choke-point behavior, that is, progressive narrowing during inspiration that produces inspiratory flow limitation. As inspiration progresses, the pharynx narrows progressively, and the resulting inspiratory airflow is reduced and limited, such that progressive decreases in downstream pressure (supraglottic pressure) fail to produce commensurate increases in airflow. High upper airway resistance occurs in episodes consisting of a series of breaths, the majority of which display inspiratory flow limitation. During these episodes of high upper airway resistance, the arterial $O_2$ may fall and the arterial $CO_2$ rise.

Sleep induced alveolar hypoventilation can be caused by high upper airway resistance. This is commonly seen in children and is probably the most common presentation of sleep disordered breathing in that age group. The disorder also occurs commonly in adults and produces symptoms comparable to sleep apnea, such as, sleepiness, fatigue, depression, cognitive impairment, impotence, muscle pains and headaches. Another feature of high upper airway resistance is that duration of inspiration may be prolonged compared to the duration of expiration. Furthermore, the intra-thoracic pressure may become quite negative. These two changes imply that the respiratory muscles develop substantial force and that the heart is exposed to large sub-atmospheric pressures which dilate it and act as a pre-load and after-load on the heart. These large sustained pressures can have adverse effects on cardiac rhythm and cardiac function. In addition the existence of obstructive hypoventilation can lead to respiratory failure with an increase in arterial $CO_2$ and consequent cerebral vascular alterations leading to prominent headaches.

During inspiratory flow limitations caused by pharyngeal narrowing, the airflow is observed to be either constant or decreasing. A highly compliant tube that displays flow limitation, for example, a Starling resistor will display constant flow with a constant upstream pressure and a progressively declining downstream pressure. However, in some cases in humans and other animals, progressive decreasing downstream pressure actually causes a reduction in airflow, referred to as negative effort dependence or negative pressure dependence. In this pattern, airflow quickly rises to a peak at the beginning of inspiration and then declines subsequently during inspiration. Such negative effort dependence is thought to reflect changes in the mechanics of the constricting pharyngeal segment caused by distortion of more downstream segment or segments which, in turn, alters the mechanical behavior of the upstream segment through mechanical interdependence of the pharyngeal wall.

Traditional approaches to detection of high upper airway resistance are based on the idea that above a certain limit, the upper airway restricts airflow to a constant rate, independent of the driving pressure like a Starling resistor. Therefore, the traditional approaches to detection of resisted breathing are based on quantifying the flatness of the breaths. Various mathematical approaches are used to generate measures of flatness with the greater amount of flatness indicating a greater amount of resisted breathing. However, the inspiratory portions of resisted breaths are not exactly flat, meaning that relying on traditional methods can cause problems when detecting upper airway resistance.

SUMMARY

There is provided a method and apparatus for detecting resisted breathing of a patient. An airflow signal corresponding to the breathing of the patient is obtained. A section corresponding to inspiration within the airflow signal is determined. The section corresponding to inspiration has a front portion and a middle portion. A peak value of the front portion is determined. The peak value of the front portion is compared with a value representing the airflow of the middle portion. The presence of resisted breathing is determined based on the comparison between the peak value of the front portion with a value representing the airflow of the middle portion.

There is provided a method of calculating a baseline flow value of a patient. An airflow signal corresponding to the breathing of the patient is obtained. A series of data points from the airflow signal is obtained, in which each of the series of data points represent the airflow volume of the patient at a point in time. The baseline flow value is set to the mode of the data points.

There is provided a method of determining a peak inspiration of an airflow wave corresponding to the breathing of a patient. A series of sequential points corresponding to the airflow signal is obtained. Each of the series of sequential points corresponds to an airflow value. The airflow value corresponding to each successive point in the series of sequential points is determined. The sequential points are analyzed in sequential order so that the sequential points are divided into analyzed points and non-analyzed points. The point having the greatest airflow value of the analyzed points is stored as a maximum point. The maximum point is set as the point of peak inspiration when the airflow value of the series of sequential points drops more than a threshold value below the greatest airflow value corresponding to the maximum point.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Figure 1:
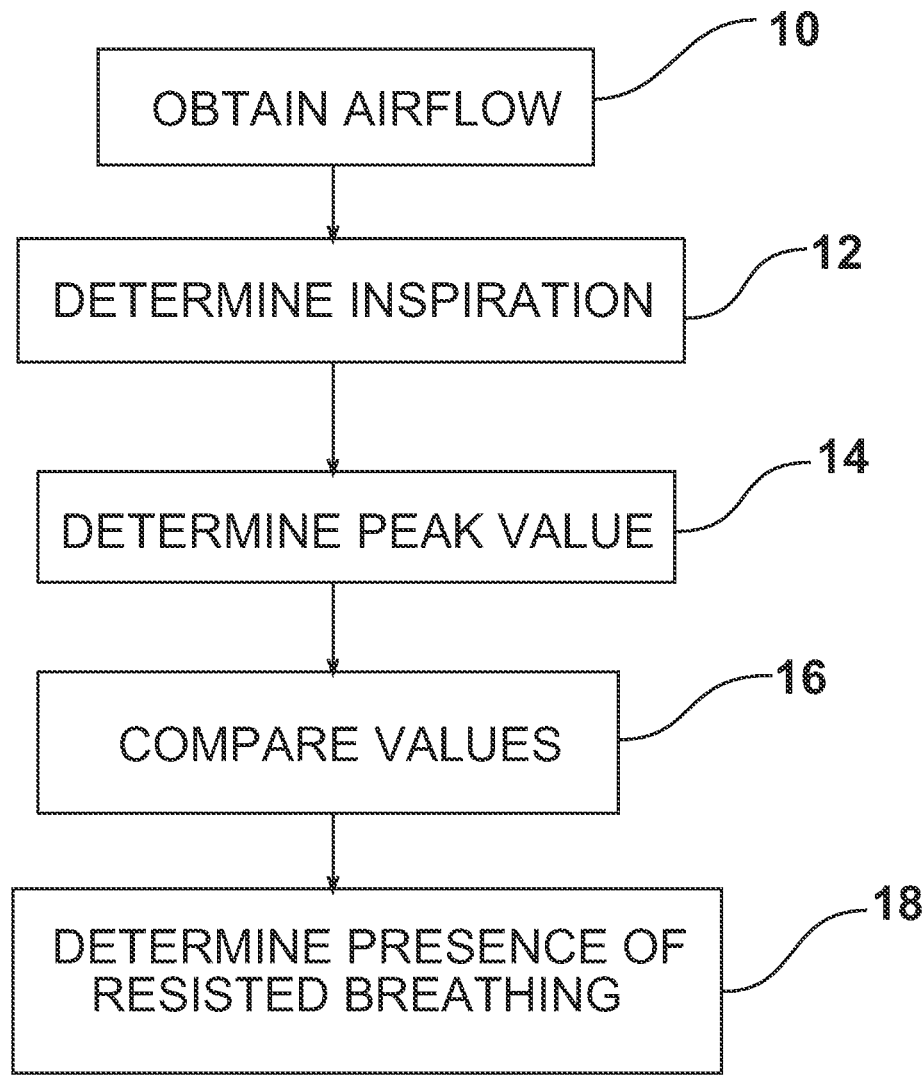
FIG. 1 is a diagram showing a method for detecting resisted breathing of a patient.

FIG. 1 shows a method for detecting resisted breathing of a patient. At step 10, an airflow signal corresponding to the breathing of the patient is obtained. At step 12, a section corresponding to inspiration within the airflow signal is determined. The section corresponding to inspiration has a front portion and a middle portion. At step 14, a peak value of the front portion is determined. At step 16, the peak value of the front portion is compared with a value representing the airflow of the middle portion. At step 18, the presence of resisted breathing is determined based on the comparison between the peak value of the front portion with a value representing the airflow of the middle portion.

A pressure signal may be obtained from a pair of tubes or cannula placed in the naris to identify periods of resisted breathing. During inspiration, there is a slight decrease in pressure in the naris that is detected by the negative arm of a sensitive pressure transducer. When this pressure signal is printed, upward deflections of the signal indicate inspiration.

Figure 2:
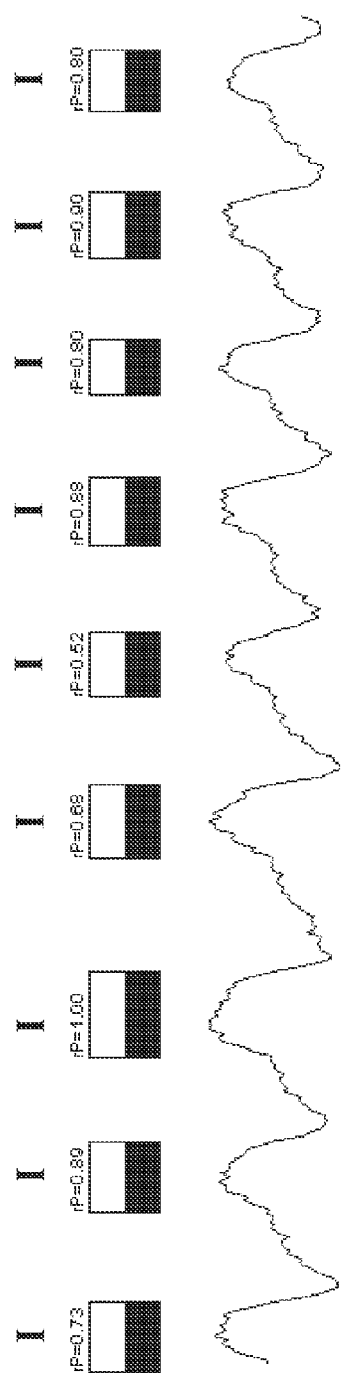
FIG. 2 is an example waveform showing normal breathing.

FIG. 2 shows an example of nasal pressure during normal breathing. The panel contains 30 seconds of data with periods of inspiration being the upward peaks and expiration being the downward troughs. The bars denoted by the reference character I above the pressure signal indicate periods of inspiration. The baseline or zero flow level is intermediate between the two extremes and is seen as flattened regions at the end of expiration.

Figure 3:
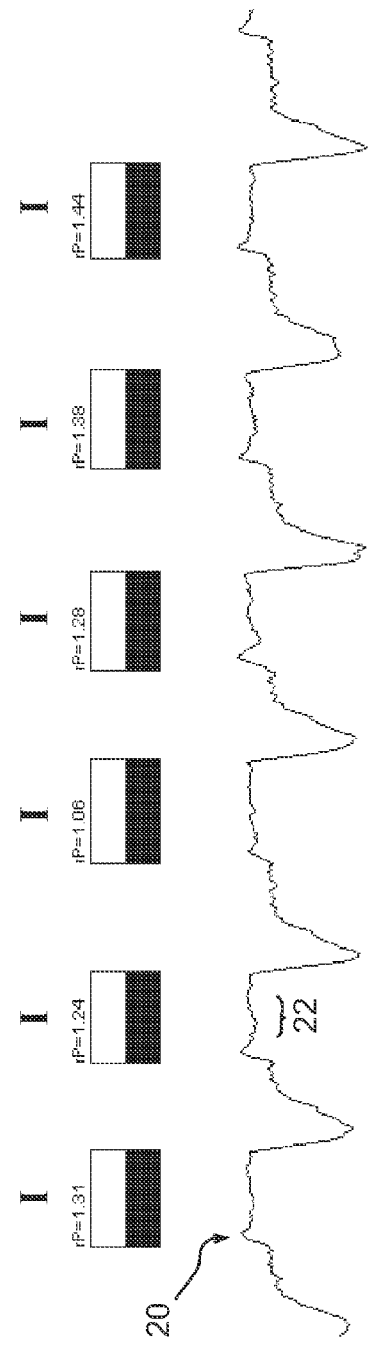
FIG. 3 is an example waveform showing resisted breathing.

During resisted breathing when the upper airway is narrowed, lower airflow rates are achieved during inspiration and breaths appear flattened and often elongated. FIG. 3 shows an example of resisted breathing. Resisted breathing contrasts with normal breathing in several ways: the breaths are longer, the inspiratory profile is flattened, and the fraction of total breath time spent in inspiration increases. The bars denoted by the reference character I above each breath indicate inspiratory portions of each breath. The inspiratory portions of the resisted breaths in FIG. 3 are not exactly flat. There is instead a peak 20 at the beginning of inspiration and a small reduction in airflow in the middle denoted generally by 22. The tops of the breaths often have a concave shape rather than a flat top. The reduction in flow rate during the middle of the breath occurs while inspiratory effort is at its maximum. This has been referred to as "negative effort dependence". It follows that a negative effort dependence of greater magnitude indicates a greater severity of high upper airway resistance.

The method of FIG. 1 classifies resisted breathing using a measure of the severity of negative effort dependence. This may be achieved by comparing the flow at the beginning of the breath with that in the middle. In some embodiments, a ratio of the peak flow of the first third of the breath to the peak flow in the middle third is calculated. One may call this the "front-mid-peak ratio". FIGS. 2 and 3 show this ratio printed above each breath.

The resisted breaths have ratios greater than one while the normal breaths have ratios less than one. In this case, the front-mid-peak ratios span from 0.5 to 1.5 representing normal through highly resisted breaths, respectively.

The fraction of breaths with a high front-mid-peak ratio is a measure of the amount of resisted breathing the patient endures during an analysis period, such as through the night. It may be used as an index of the severity of high upper airway resistance. In some embodiments, the fraction of breaths with a ratio greater than 1.05 is used and an index of around 15% is a practical threshold for clinical purposes. In other embodiments, other thresholds around 1 may be used and different indexes may be used. The threshold value may be chosen based on the level of resisted breathing of the patient—at which the algorithm determines the presence of resisted breathing for a breath. If a higher threshold value is chosen, then higher levels of resisted breathing will need to occur before resisted breathing for a breath is determined. If a lower threshold value is chosen, then lower values of resisted breathing will be sufficient to determine resisted breathing for a breath. The index value determines the severity of high upper away resistance based on the percentage of breaths in which resisted breathing is determined. If the index value is lower, then fewer resisted breaths need to be determined before resisted breathing over the duration of the analysis period is reported. If the index value is higher, then more resisted breaths need to be indicated before resisted breathing for the duration of the analysis period is reported. For example, an index threshold of 0% would mean that resisted breathing would be reported if any resisted breaths, as determined by the threshold ratio, occurred during the analysis period.

The peak 20 at the beginning of resisted breaths is an important indicator of resistance. The ratio is easily generated once the period of inspiration has accurately been identified. In some embodiments, the peak flow in the first third may be compared to the average value of flow in the middle third. In other embodiments, the peak flow may be compared to the middle value of the middle third. The inspiration may also be divided into sections other than thirds, provided that the peak 20 at the beginning of the resisted breath lies in the first section and the second section contains values generally during the reduction of airflow denoted by 22.

A challenge in quantifying resisted breathing is to detect the small flattened breaths that are just marginally above the baseline. Small changes in the baseline, such as drift in measurement equipment, make use of a simple threshold unreliable. Searching for "breath-like fluctuations" in the airflow waveform independently of the baseline value is a first step in finding airway resistance.

Figure 4:
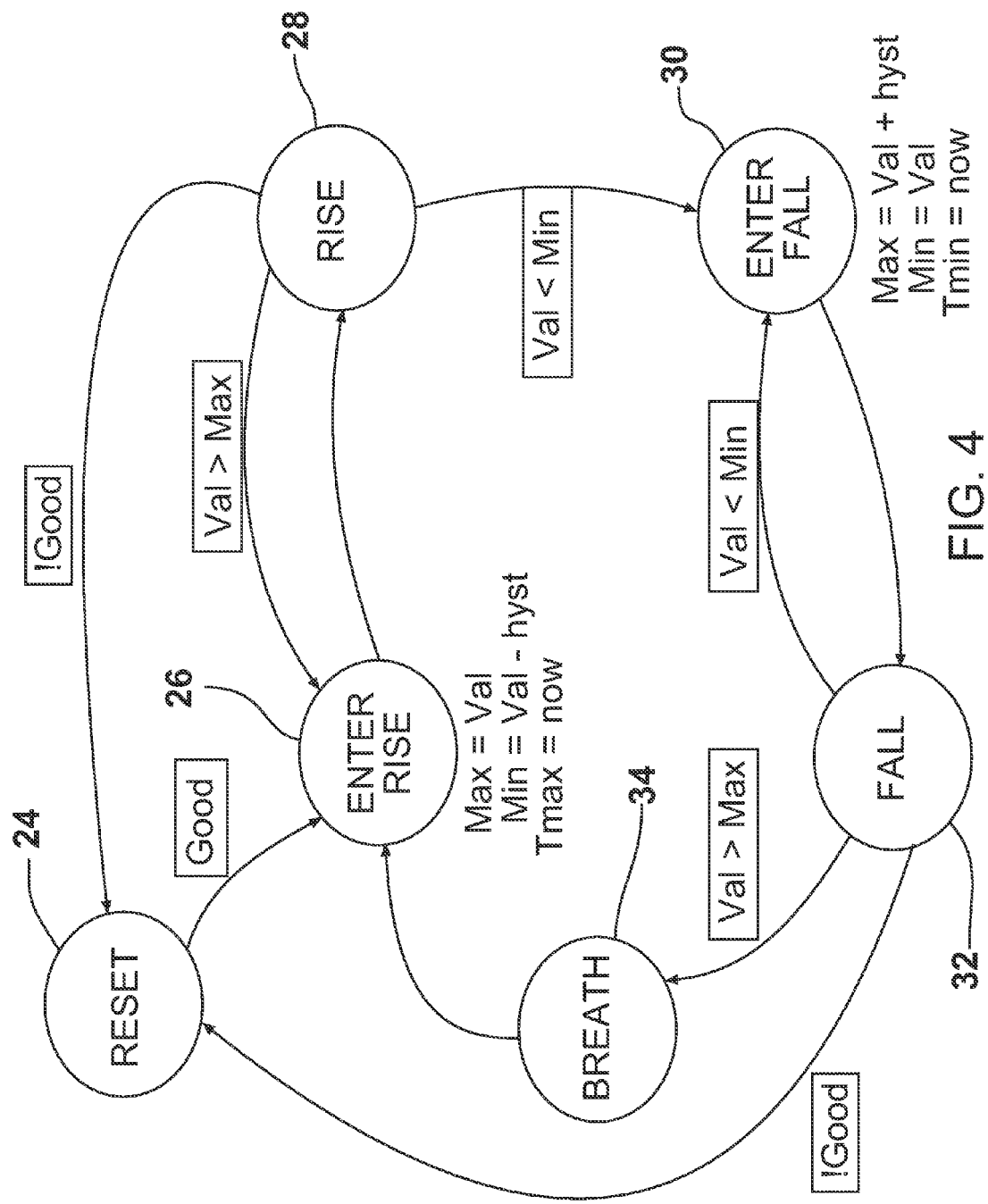
FIG. 4 is a flow diagram showing a method of finding breaths in a waveform signal.

A method of searching for breath-like fluctuations is shown in FIG. 4. The airflow signal is read one data point at a time, first searching for a big peak then followed by a big trough. The most recent value read by the algorithm is called the present value. Each data point is associated with a time value. The algorithm may be conceptualized as a little machine that moves along the flow signal first looking for a peak then looking for a trough. The transition from searching for one feature to another is a state change. A variable within the machine defines the present state of the machine, therefore, it is called a state machine. Additional variables, a maximum pressure value Max, a minimum pressure value Min, a maximum time value Tmax, and a minimum time value Tmin completely define the state of the machine at any time. The definition of the possible states and possible transitions between states completely defines how the state machine will react to input data as shown schematically in FIG. 4.

The machine starts in a reset state 24 and then proceeds through to other states as certain conditions are met. When in the reset state 24 and valid pressure data is encountered, the state changes to an enter_rise state 26. On entering the enter_rise state 26, other state variables are initialized as indicated below the enter_rise node. There are three initial variables in the enter_rise state 26, the maximum pressure value, the minimum pressure value and the maximum time value. In the enter_rise state 26 the maximum pressure value is set to the present value, the minimum pressure value is set to the present value minus a defined value, and the maximum time value is set to the present sample time. After the variables are initialized, the state unconditionally changes to a rise state 28 as indicated by an arrow with no condition criteria. There are three ways to leave the rise state 28 as indicated by the three arrows that exit the state. Each arrow has a condition that would cause that path to be followed. For example, if the present value is more than the maximum pressure value, the machine will transition to the enter_rise state 26 where the maximum pressure value is set to the present value, the minimum value is set to the present value minus a defined value, and the time maximum value is set to the present sample time. Again, the machine would then unconditionally return back to the rise state 28. If the present value is less than the minimum pressure value, the state machine will move to an enter_fall state 30. Following the enter_fall state 30, the state unconditionally changes to a fall state 32. If the present value is less than the minimum pressure value, then the minimum pressure value is set to the present value, the maximum pressure value is set to the present value minus the defined value and a variable time minimum is set to the present sample time. If the present value becomes greater than the maximum pressure value, the state completes a breath 34, and the time maximum and the time minimum are saved. The maximum pressure value and the minimum pressure value may also be saved. Following the completion of the breath, the state unconditionally changes back to the enter_rise state 26 and the process repeats.

The state machine continues operating in this manner: reading through the flow signal, changing states accordingly, and executing any code as defined by a state. The machine spends most of its time in either the rise state 28 or the fall state 32. For example, if the machine is in the rise state 28, it will continue to stay there as long as it keeps encountering values greater than the minimum pressure value but lower than the maximum pressure value. However, if the machine encounters a value lower than the minimum pressure value it will transition to the enter_fall state 30 and then to the fall state 32 where it is often equally stable for some time. The states enter_rise 26 and enter_fall 30 are not stable states but are instead transition states that adjust some state variables and then quickly, and unconditionally, move to the more stable states of rise 28 and fall 32.

The minimum and maximum values are thresholds used for state transitions but they are always separated by the defined value, which is also called the hysteresis value. This value is just less than the range of the smallest expected breath like waveform but greater than any noise that may be present. In the rise state 28 in FIG. 4 for example, if a value is encountered that is higher than the maximum, the maximum is reassigned to the new maximum value and minimum raised accordingly. In this manner, new values higher than the present maximum ratchet the two values up. If eventually, a value less the minimum is encountered, the state changes as dictated by the state machine schematic. The hysteresis value is chosen to reduce erroneously identifying minor fluctuations as breaths, but still correctly identify even small breaths.

Unlike the transition from rise state 28 to fall state 32, there is not a direct path back from the fall state 32 back to the rise state 28 but rather a transition through the state labeled breath 34. This is a transitional state in which a breath waveform is logged. The time of the minimum and maximum pressure values encountered are saved for the next stage of processing.

Generally the machine is in one of the two stable states, which is what determines whether it is searching for a peak (rise state 28) or a trough (fall state 32). These two main states are illustrated in the breath like wave form in FIG. 5 showing the connection between the waveform and the state machine.

Figure 5:
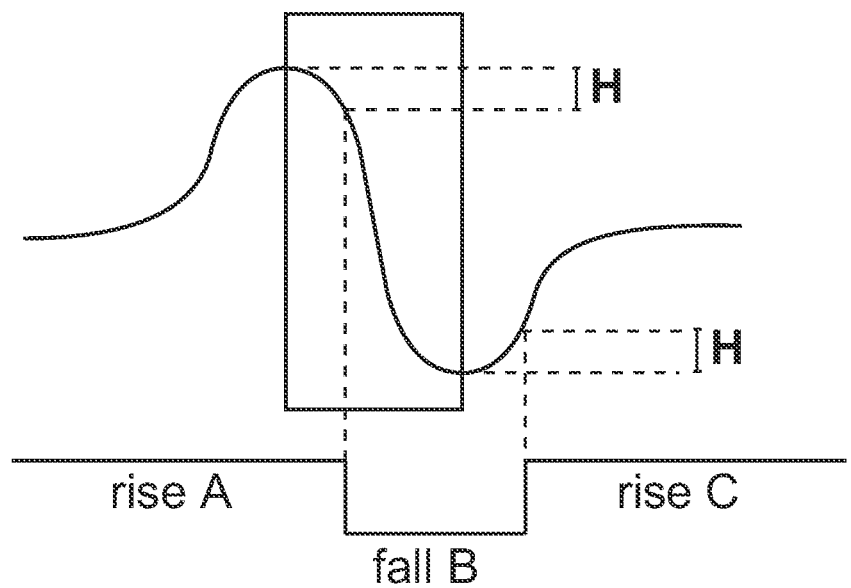
FIG. 5 shows an example of a breath pattern.

FIG. 5 is a schematic showing what is meant by a breath-like fluctuation which is a peak followed by a trough representing inspiration and expiration, respectively. The algorithm has been designed to identify these dominant features of the signal. The hysteresis value is indicated in FIG. 5 by the two small bars H just after the peak and after the trough. The state machine shown in FIG. 4 will not detect fluctuations with heights smaller than H. Below the breath like waveform is a trace showing the state of the state machine. Three states are shown in the waveform. The section A corresponds to a rise in the state machine shown in FIG. 4, that is, where the state machine is in the rise state 28. Section B corresponds to a fall in the state machine, that is, where the state machine is in the fall state 32. Section C corresponds to a second rise in the state machine. The machine remains in the rise state 28 until the signal has fallen to less than the maximum minus the hysteresis value denoted in FIG. 5 by H, confirming the signal is really falling. Similarly, exit out of the fall state is not confirmed until the signal is above the minimum plus the hysteresis value H. In each of the stable states, this is how the use of the hysteresis value provides an element of noise immunity.

The state machine described in FIG. 4 generates a list of regions in the flow signal with the simple peak trough morphology and of greater amplitude than the hysteresis value. But some real breaths with more complex shape may cause multiple triggering of the state machine. A set of rules may be used to combine multiple waveforms together into single breaths as required. These rules are based on expected physiological limits. In some embodiments, the five rules for combining multiple waveforms are used. First, the list of breath waveforms is modified using a reverse pass of the list with three rules that combine inspiratory components together:
 1) combine two breaths with less than 200 ms separation between them;
 2) combine two breaths if the range of the first is less than half the range of the second, and the two breaths are no more than 500 ms apart; and
 3) combine two breaths if the minimum value of the first is above the midpoint value of the second and two breaths are no more than 3 seconds apart.

Next, the list of breath waveforms is modified using a forward pass of the list with two rules that combine expiratory components together:
 4) combine two breaths if the range of the second is less than half the range of the second, and the two breaths are no more than 500 ms apart; and
 5) combine two breaths if the maximum value of the second breath is less than the midpoint of the first breath and the two breaths are no more than 1 second apart.

Each breath waveform in the resulting list defines the approximate location of a physiological breath but does not accurately define the physiological phases of the breath. Each breath waveform contains the pressure value and time of a crest and a trough with the crest always preceding the trough. The pressure value of the crest is the maximum and the pressure value of the trough is the minimum. The range of a breath waveform is the difference in value between the maximum pressure value and the minimum pressure value within the breath waveform. A time separation between two breath waveforms is the difference in time between the time of the crest of the second breath waveform and the time of the trough of the first breath waveform. The midpoint value of a breath waveform is half the difference between the maximum inspiration value and the minimum expiration value.

In other embodiments, other rules may be used to combine multiple waveforms into single breaths based on common or expected breath forms. The rules used to combine multiple waveforms are based on physiological characteristics of breath forms.

Once valid breaths have been identified, the true extent of the inspiratory phase of the respiratory cycle is determined for each breath. The previous stage only produces the location of the peak inspiration but not beginning and end of inspiration. Inspiration starts when flow rises above a baseline and ends when it drops below the baseline. Therefore at this stage of processing, the baseline or zero flow value is required. The baseline value is determined from the data.

Figure 6:
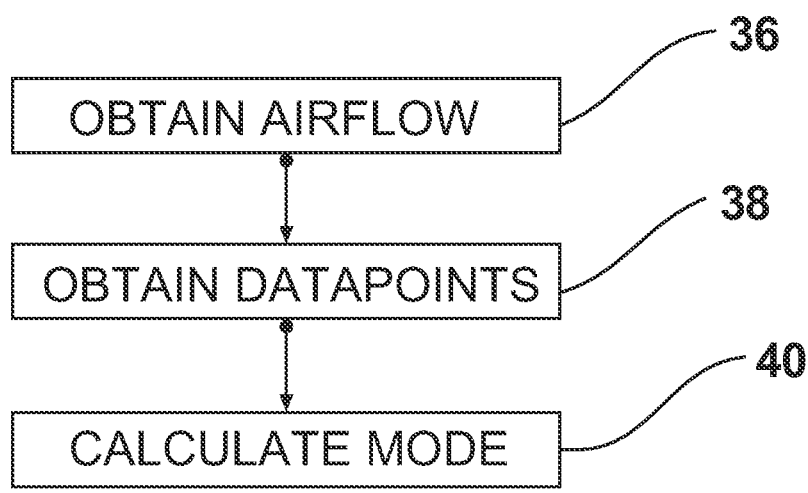
FIG. 6 is a flow diagram representing a method of detecting a baseline value of a waveform signal.

As shown in FIG. 6, at step 36 an airflow signal is obtained which corresponds to the breathing of the patient. At step 38, a series of data points are obtained from the airflow signal. At step 40, the baseline flow value is set to the mode of the data points.

Often during normal levels of ventilation, there are brief periods with no flow at the end of expiration before the next inspiration. This is seen in the flow tracings in FIGS. 2 and 3 but is especially pronounced in FIG. 3. This is the most common value in the flow signal and is obtained by calculating the mode of the histogram of the flow signal. Values in the flow signal can be calculated for a period of a few minutes to find a local baseline or can be calculated over a longer period of time to find a global baseline value. The local baseline value may be used as the baseline value when the local baseline value is close enough to the global value to allow for accurate measurements of periods of inspiration. In some cases the baseline may change during the night, such as, for example, during use of an automatically adjusting CPAP machine. Changes in the baseline may be calculated based on variations of local baseline values.

Having obtained the baseline flow value, begin and end inspiration is found for each breath by first starting with the peak value. Data values are searched backwards from the peak until the baseline is reached to find the begin inspiration. End inspiration is similarly found by searching forward.

Having identified the extent of inspiration for each breath, the front-mid-peak ratio for each breath may be computed by dividing inspiration into three equal sections, computing the peak value of the first two sections, and then calculating the ratio. The index for the complete night is calculated by measuring what fraction of breaths have ratios that exceed a threshold to define a resisted breath, such as 1.05.

Figure 7:
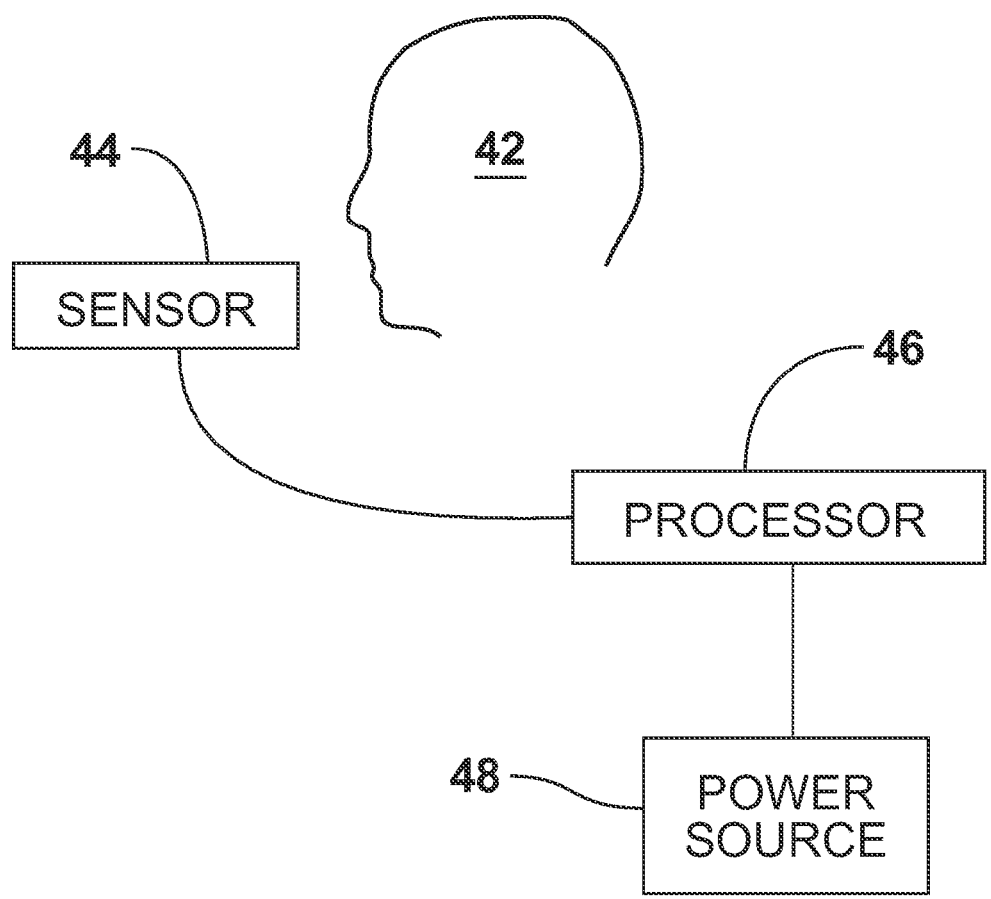
FIG. 7 shows a block diagram representing an apparatus for detecting resisted breathing of a patient.

FIG. 7 shows an apparatus for detecting the resisted breath of a patient 42. A sensor 44 is connected to a processor 46. The processor 46 is connected to a power source 48. The sensor 44 detects an airflow signal from the patient 42. The processor 44 analyzes the airflow signal detected by the sensor 44. For example, the processor may analyze the airflow signal by performing the method steps shown in FIGS. 1 and 6. The processor may be any device that can perform an analysis of the airflow signal and determine the existence of resisted breathing of the patient 42. The processor may output information to a screen, may store information in memory or may send information to a different location. For example, the data may be sent to a second processor, such as a desktop computer, for further analysis or for data storage. The sensor may be any sensor capable of detecting an airflow signal corresponding to the breathing of a patient. In some embodiments, the sensor may be a pair of tubes or cannula placed in the naris of a patient. In some embodiments, the sensor may be a pneumotachograph in series with a hose on a CPAP machine. In some embodiments, the sensor may be a pressure sensor for detecting the oral airflow of a patient.

The airflow signal is not limited to a pressure signal, as described in the embodiments above. Any type of airflow signal corresponding to the breathing of a patient may be used. For example, the airflow signal may correspond to the rate of airflow to and from the lungs, such as may be obtained from a pneumotachograph in series with a hose on a CPAP machine. In some embodiments, the airflow signal may be an oral airflow pressure signal.

Immaterial modifications may be made to the embodiments described here without departing from what is covered by the claims. In the claims, the word "comprising" is used in its inclusive sense and does not exclude other elements being present. The indefinite article "a" before a claim feature does not exclude more than one feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A method for detecting resisted breathing of a patient, comprising the steps of:
    obtaining an airflow signal corresponding to the breathing of the patient by sensing airflow of the patient with a sensor connected to a processor;
    the processor carrying out an algorithm that instantiates a state machine;
    the state machine operating on the airflow signal to change the state of the state machine, the state machine being defined at least by a maximum value of the airflow signal and a minimum value of the airflow signal;
    determining a section of the airflow signal corresponding to inspiration within the airflow signal, the section corresponding to inspiration having a front portion and a middle portion;
    determining a peak value of the front portion as the maximum value of the airflow signal after the state machine has operated on the section of the airflow signal corresponding to inspiration;
    comparing the peak value of the front portion with a value representing the airflow of the middle portion; and
    determining the presence of resisted breathing based on the comparison between the peak value of the front portion with the value representing the airflow of the middle portion.

2. The method of claim 1 in which the value representing the airflow of the middle portion is a peak value of the middle portion.

3. The method of claim 2 in which the step of comparing the peak value of the front portion with the value representing the airflow of the middle portion further comprises finding a front-mid-peak ratio of the peak value of the front portion with the peak value of the middle portion.

4. The method of claim 3 further comprising the step of reporting the presence of resisted breathing when the value of the front-mid-peak ratio is greater than 1.05.

5. The method of claim 1 in which the front portion is the front third of the section corresponding to inspiration and the middle portion is the middle third of the section corresponding to inspiration.

6. The method of claim 1 in which the airflow signal corresponding to the breathing of the patient comprises a pressure signal obtained from a naris of a patient.

7. The method of claim 1 in which the step of determining the section corresponding to inspiration within the airflow signal further comprises:
    finding a point of peak inspiration of the airflow signal;
    determining a baseline value of the airflow signal, the airflow signal oscillates around the baseline value with a set of crests above the baseline value and a set of troughs below the baseline value; and
    setting the section corresponding to inspiration as a crest of the set of crests above the baseline value, the crest containing the point of peak inspiration.

8. The method of claim 7 in which finding the point of peak inspiration of the airflow signal further comprises the following steps:
- obtaining a series of sequential points corresponding to the airflow signal, each of the series of sequential points corresponding to an airflow value;
- determining the airflow value corresponding to each successive point in the series of sequential points;
- analyzing the sequential points in sequential order with the processor, the sequential points being divided into analyzed points and non-analyzed points and setting a maximum point in the state machine as the point having the greatest airflow value of the analyzed points;
- for each section of the airflow signal corresponding to a breath, setting the maximum point as the point of peak inspiration when the airflow value of the series of sequential points drops more than a threshold value below the greatest airflow value corresponding to the maximum point.

9. The method of claim 7 which the baseline is calculated using the following steps:
- obtaining an airflow signal corresponding to the breathing of the patient;
- obtaining a series of data points from the airflow signal, each data point of the series of data points representing the airflow volume of the patient at a point in time and each series of data points having a mode; and
- setting the baseline flow value to the mode of the data points.

10. The method of claim 9 further comprising dividing the series of data points into flow value intervals and in which the step of setting the baseline flow value to the mode of the data points further comprises setting the baseline flow value to a data point contained in the flow value interval containing the most data points.

11. The method of claim 1 in which the airflow signal corresponding to the breathing of the patient comprises a rate of airflow to and from the lungs of a patient.

12. The method of claim 1 in which the airflow signal corresponding to the breathing of the patient comprises an oral airflow pressure signal.

13. A method of determining a peak inspiration of an airflow wave corresponding to the breathing of a patient, comprising the steps of:
- obtaining a series of sequential points corresponding to the airflow signal by sensing airflow of the patient with a sensor connected to a processor, each of the series of sequential points corresponding to an airflow value, the series of sequential points having a mode;
- the processor carrying out an algorithm that instantiates a state machine;
- the state machine operating on the airflow signal to change the state of the state machine;
- determining the airflow value corresponding to each successive point in the series of sequential points;
- analyzing the sequential points in sequential order with the processor, the sequential points being divided into analyzed points and non-analyzed points and changing the state of the state machine by storing the point having the greatest airflow value of the analyzed points as a maximum point;
- setting a baseline flow value within the processor to the mode of the data points and determining an inspiratory phase of the breathing of the patient by identifying where the airflow signal crosses the baseline flow value, to determine each section of the airflow signal corresponding to a breath; and
- for each section of the airflow signal corresponding to a breath, setting the maximum point as the point of peak inspiration when the airflow value of the series of sequential points drops more than a threshold value below the greatest airflow value corresponding to the maximum point.

* * * * *